United States Patent
Wolf et al.

(10) Patent No.: US 8,139,232 B2
(45) Date of Patent: Mar. 20, 2012

(54) MULTIPLE MEASUREMENT TECHNIQUES INCLUDING FOCUSED BEAM SCATTEROMETRY FOR CHARACTERIZATION OF SAMPLES

(75) Inventors: Robert Gregory Wolf, Hackettstown, NJ (US); Michael J. Kotelyanskii, Chatham, NJ (US)

(73) Assignee: Rudolph Technologies, Inc., Flanders, NJ (US)

( * ) Notice: Subject to any disclaimer, the term of this patent is extended or adjusted under 35 U.S.C. 154(b) by 457 days.

(21) Appl. No.: 12/309,749

(22) PCT Filed: Jul. 27, 2007

(86) PCT No.: PCT/US2007/016842
§ 371 (c)(1),
(2), (4) Date: Jul. 7, 2009

(87) PCT Pub. No.: WO2008/013909
PCT Pub. Date: Jan. 31, 2008

(65) Prior Publication Data
US 2009/0279090 A1    Nov. 12, 2009

(51) Int. Cl.
*G01B 11/14* (2006.01)
*B01J 4/00* (2006.01)

(52) U.S. Cl. .................................. 356/625; 356/369

(58) Field of Classification Search .................. None
See application file for complete search history.

(56) References Cited

U.S. PATENT DOCUMENTS

| | | | |
|---|---|---|---|
| 5,166,752 A | 11/1992 | Spainer et al. | 356/369 |
| 6,175,416 B1 | 1/2001 | Maris et al. | 356/381 |
| 6,429,943 B1 | 8/2002 | Opsal et al. | 356/625 |
| 6,483,580 B1 | 11/2002 | Xu et al. | 356/300 |
| 6,657,736 B1 | 12/2003 | Finarov et al. | 356/625 |
| 6,713,753 B1 | 3/2004 | Rovira et al. | 250/225 |
| 6,721,052 B2 | 4/2004 | Zhao et al. | 356/369 |
| 7,050,178 B2 | 5/2006 | Morath et al. | 356/630 |
| 7,206,070 B2 | 4/2007 | Opsal | 356/369 |
| 2006/0103844 A1 | 5/2006 | Opsal | 356/369 |

OTHER PUBLICATIONS

Thompson, et al., "A Logic Nanotechnology Featuring Strained-Silicon", IEEE Electron Device Letters, vol. 25, No. 4. (Apr. 2004), (3 pages).

*Primary Examiner* — Gregory J Toatley
*Assistant Examiner* — Amanda Merlino
(74) *Attorney, Agent, or Firm* — Harrington & Smith (57) ABSTRACT

A system for monitoring thin-film fabrication processes is herein disclosed. Diffraction of incident light is measured and the results are compared to a predictive model based on at least one idealized or nominal structure. The model and/or the measurement of diffracted incident light may be modified using the output of one or more additional metrology systems.

21 Claims, 6 Drawing Sheets

MULTIPLE MEASUREMENT TECHNIQUES INCLUDING FOCUSED BEAM SCATTEROMETRY FOR CHARACTERIZATION OF SAMPLES

TECHNICAL FIELD

This invention relates generally to measurement of samples and, more specifically, relates to focused beam scatterometry and other metrology measurements of samples.

BACKGROUND OF THE INVENTION

With the increasing integration density and operating frequencies of microelectronic devices, manufacturing processes for these devices require the ability to measure dimensions of submicron structures that make up the devices and thickness of the thin films deposited on, around, or under the structures. These measurements are performed during the numerous lithography, etching, and thin-film deposition steps of the manufacturing process. New transistor generations are built of non-planar structures defined during processing of multilayered films, and these generations require metrology measurements beyond just measuring the multilayered films at each process step.

Optical measurements provide fast, accurate, non-destructive, and relatively inexpensive analysis techniques. As sample structure dimensions become smaller than or comparable to the light wavelength, simple imaging such as microscopy is not possible, and the measurements require analysis of the intensity and/or the polarization state of the light scattered off the sample structure. The simplest analysis and greatest sensitivity are achieved when periodic arrays of sample structures are measured.

Non-destructive, non-contact, small spot, high throughput and high accuracy method and apparatus are necessary for accurate characterization of the dimensions of the sub-micron structures and the thin films surrounding the structures.

BRIEF DESCRIPTION OF THE DRAWINGS

The foregoing and other aspects of embodiments of this invention are made more evident in the following Detailed Description of Exemplary Embodiments, when read in conjunction with the attached Drawing Figures, wherein.

DETAILED DESCRIPTION OF EXEMPLARY EMBODIMENTS

Wherever possible, the standard definitions of words used in this specification have been adopted. However, to minimize misunderstanding the following words are defined with added particularity: "characteristic", "parameter", "model", "sample", and "structure". It is understood that the preceding words have generally understood meanings and to the extent possible, those meanings have been followed. The additional definitions found below are for clarification purposes only.

Sample—a sample may be any thing having one or more structures or materials deposited or formed thereon. As used herein, the terms "sample", "substrate", and "wafer" may be used interchangeably.

Structure—a structure is a thing on the sample or part of the sample that is being measured. Note that the term "structure" may be used interchangeably at times to denote an item such as, e.g. a grating, line or a layer that is formed on the sample. Further, it should be recalled that samples are typically formed of multiple layers and that layers may be formed over, under, adjacent, or apart from one or more objects such as gratings or lines.

Characteristic—a characteristic is an objective feature of a structure on the sample that may be a dimension, a geometry, a spacing or an alignment.

Parameter—a parameter is a value obtained or derived observationally (using a metrology tool) or mathematically (through solution of an appropriate model) that at least partially correlates with one or more characteristics of a sample, for example, the measured Rp/Rs ratio of a sample. Keep in mind that parameters may be measured directly, i.e. may be directly related to light intensities derived directly from the detector, but are also likely to be derived from such intensity data. Additional parameters may include, but are not limited to diffraction patterns, spectra and spectral patterns, intensities, polarization states of reflected light, an index of refraction, dopant concentration, crystalline structure, stress, strain, chemical makeup, and the like.

Model—a model is one or more equations and/or their solutions that are representative of one or more parameters of a sample under a predefined set of conditions. Conditions for a model may include by way of example and without limitation, angle of incidence, wavelength of incident light, periodicity of gratings, sidewall configuration of linear structures, or optical characteristics of materials from which the sample being modeled is fashioned. Models are used to predict what might occur for a given set of conditions.

Figure 1A:
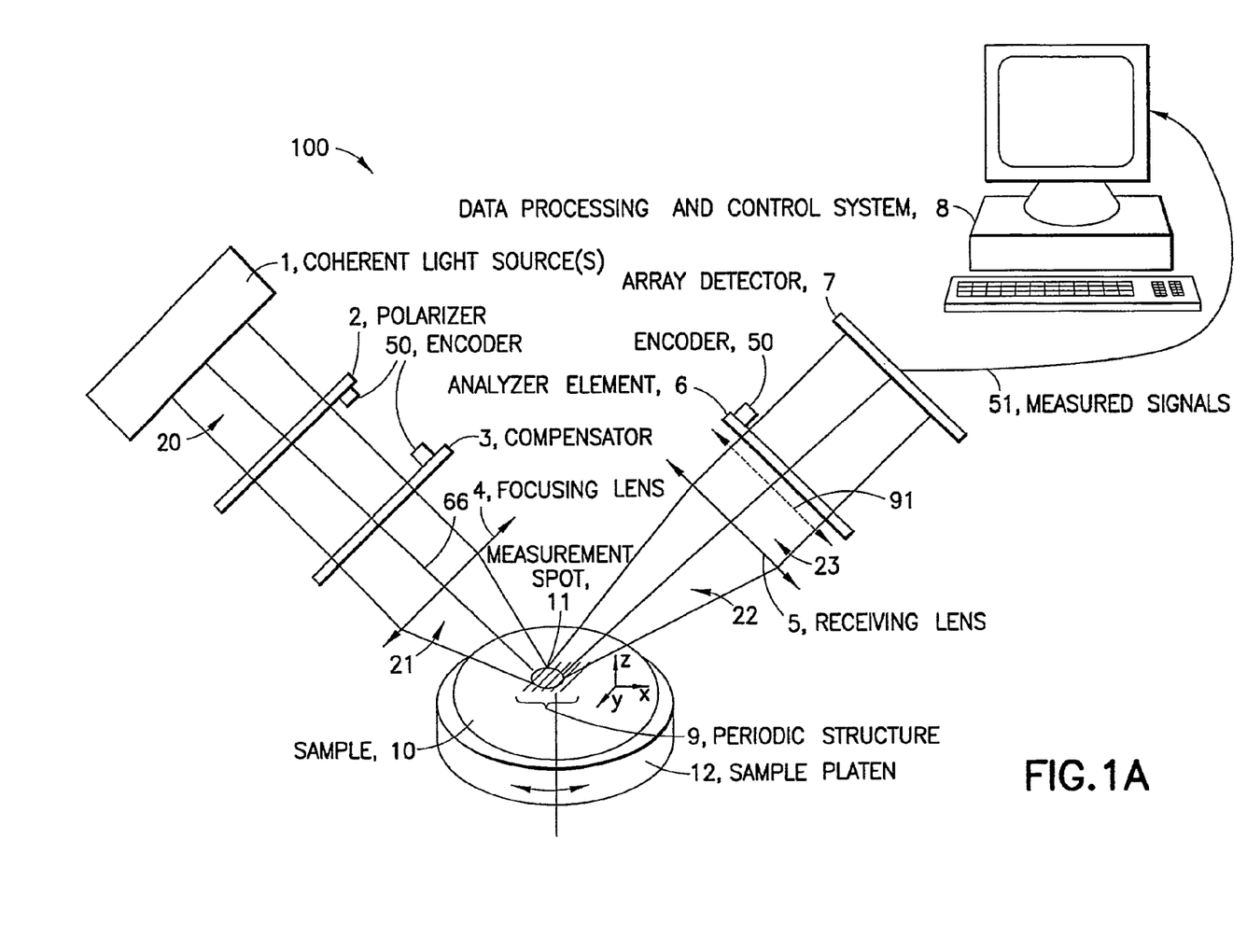
FIG. 1A is a simplified diagram of an exemplary focused beam scatterometry measurement system suitable for measuring a sample and for implementing exemplary embodiments of the disclosed invention.
Figure 1B:
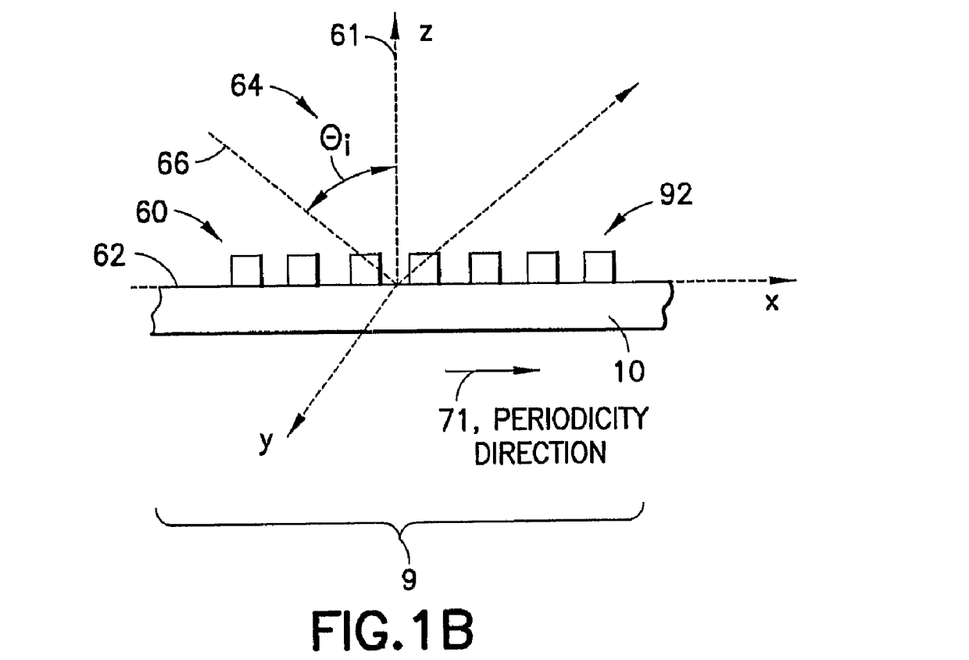
FIG. 1B is an exemplary illustration of a cross-sectional view of the sample shown in FIG. 1A.
Figure 1C:
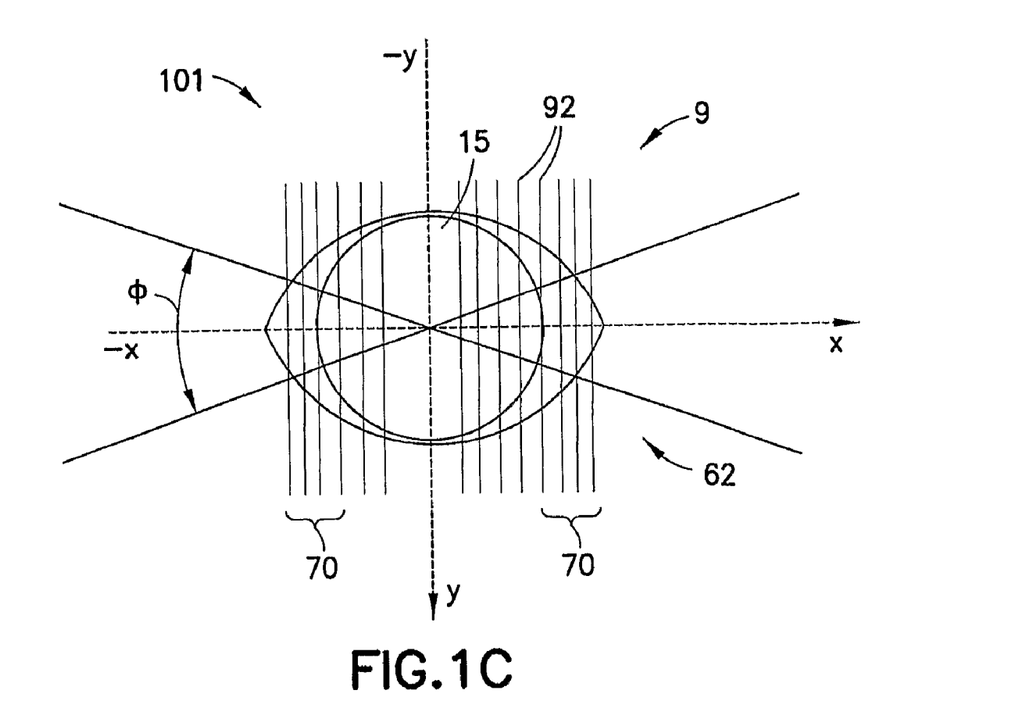
FIG. 1C is an exemplary illustration of a top view of the sample shown in FIG. 1A.
Figure 1D:
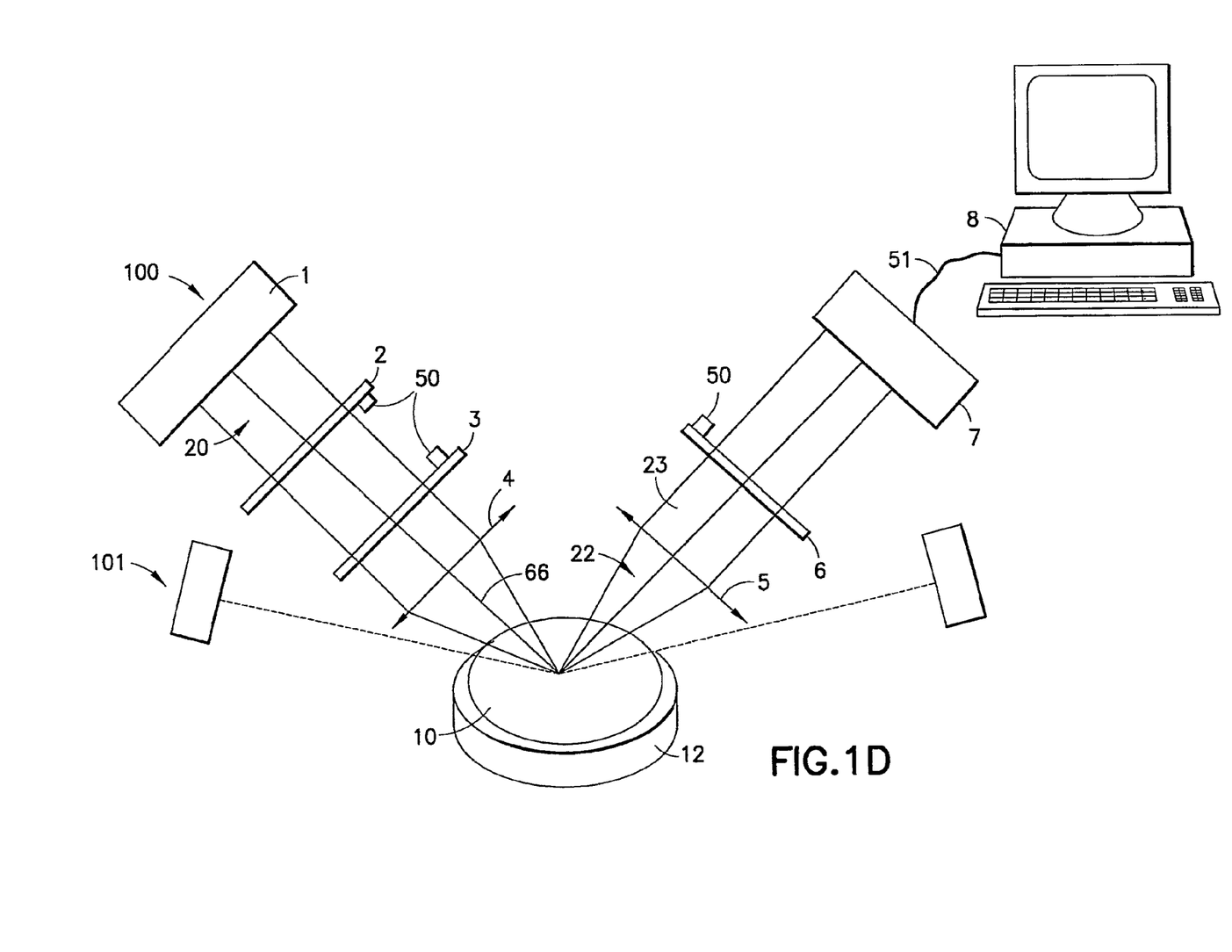
FIG. 1D is an exemplary illustration of the system of FIG. 1A as used in conjunction with a separate measurement system.

Turning now to FIGS. 1A through 1D, a simplified diagram of an exemplary focused beam scatterometry measurement system 100 is shown. FIG. 1A illustrates a system 100 suitable for implementing exemplary embodiments of the disclosed invention including, but not limited to critical dimension metrology, overlay alignment metrology, edge roughness metrology, line width metrology, and line geometry metrology. FIG. 1B illustrates a cross-sectional view of the sample 10 shown in FIG. 1A, while FIG. 1C illustrates a top view of the sample 10 shown in FIG. 1A. FIG. 1D illustrates how system 100 may be used in conjunction with other metrology or inspection systems.

System 100 has one or more coherent light sources 1, such as lasers, that produce a collimated beam 20 of light. The collimated beam 20 of light passes through a polarizer 2 and a compensator 3 and is focused to the sample 10 by the focusing optic 4. The focused beam 21 illuminates part of the periodic structure 9 within the measurement spot 11 created by the focused beam 21 on the sample 10.

A reflected beam 22 is then collected by the receiving optic 5, which converts the reflected beam 22 into a collimated beam 23. Light scattered off the sample, corresponding to the different incidence angles, is now distributed along the cross-section 91 of the collimated beam 23. This light of the collimated beam 23 passes through the analyzer element 6 and is incident upon the detector array 7. Intensity of the light detected by each pixel (not shown) of the detector array 7 corresponds to a different angle of incidence and the intensity is converted to measured signals 51. Light from the different parts of the cross-section 91 of the reflected beam 22 and the collimated beam 23 therefore hits different pixels of the detector array, thus resolving multiple incidence angles and providing capability of fast simultaneous multi-angle measurement. In an exemplary embodiment, the system 100 is designed to characterize change of both the intensity and the polarization state of the incident light after the incident light is reflected off the structure. Such a configuration was earlier described in U.S. Pat. No. 5,166,752 to Spanier et al. (which is hereby incorporated, in its entirety, by reference), in applications including the measurements of multilayered thin films, and is implemented in the Rudolph Technologies, Inc. SpectraLASER™ and Ultra™ metrology products for characterization of thin multilayered films.

The intensity of light is converted by the detector array 7 into measured signals 51. One or more of compensator 3, polarizer 2, and analyzer 6 can be rotating. Further, it should be understood that the compensator 3 is an optional element and may be omitted entirely. Alternatively, the compensator 3 may be replaced by or used in combination with a photo-elastic modulator. The rotation of the compensator 3, polarizer 2, and/or analyzer 6 changes the polarization state of the light incident on the detector array 7, and allows measurement of the ellipsometric ratio, Rp/Rs, of the reflectivities for the P- and S-polarizations as a function of the rate(s) of rotation of the rotating elements. Encoder(s) 50 on the rotating elements (e.g., one or more of compensator 3, polarizer 2, and analyzer 6) provides information to the data processing and measurement control system 8 about the position and rate of rotation of each element, in order to interpret a change of the intensity at each detector pixel, which is then converted to the Rp/Rs ratio by the data processing and control system 8 as is well known in the art. Those skilled in the art will appreciate that the system 100 described above may be operated as a scatterometer, ellipsometer, or reflectometer, among others, and that when operated as an ellipsometer may be operated in multiple static or dynamic manners. Some examples of modes of operation of the system 100 include, but are not limited to, rotating compensator ellipsometry, rotating polarizer ellipsometry, rotating analyzer ellipsometry, null ellipsometry and stokes ellipsometry and extinction ellipsometry.

Data processing and control system 8 uses measured signals 51 to identify structure parameters, based on modeling of the light scattering. Analysis is performed by calculating the Rp/Rs ratio of the scattered light for a given wavelength, incidence angle, structure orientation, and one or more model parameters associated with the structure. The measurement results may include, among others, structure pitch, layer thicknesses, critical dimensions, and sidewall angle. It will be appreciated that additional measurements or parameters may be obtained. Incidence plane 60 (see FIG. 1B) is the plane that contains the incident beam (e.g., focused light beam 21), and a vector 61, normal to the surface 62 of the sample 10. The incidence angle 64, $\theta_i$, is the angle between the incident beam (e.g., focused light beam 21) and the vector 61 normal to the surface 62. Note that incidence angle 64 could be a range of angles as defined by the focusing lens 4. In the example of FIG. 1B, the angle of incidence 109 is measured using the center or principal optical axis 66 of the focused light beam 21. Additionally, in the example of FIG. 1B, the incidence plane 60 is the x-z plane, though it is to be understood that the incidence plane 60 may be oriented at any desired angle around the normal vector 61.

U.S. Pat. No. 7,206,070 to Opsal, et. al. discloses a normal incidence ellipsometer for use in scatterometry that suffers from a coupling between polarization state and azimuthal angle in the data output from the detector of the ellipsometer. This coupling makes it difficult to differentiate variations in the output due to changes in polarization state of reflected light and those due to variations in azimuthal angle. Accordingly, Opsal et. al. must accommodate this by modeling the output of their system on a coupled basis. The alternative to this is to perform a series of fairly complicated calculations to de-couple the data.

The system 100 of the present invention avoids these pitfalls by providing data in which the polarization state of reflected light is substantially uniform over substantially the entire range of azimuthal angles at which light is incident upon the sample 10. Accordingly, models of the predicted response of the system 100 for a given set of conditions are not required to accommodate coupling between what are essential independent variables. This simplifies the model and obviates the need to de-couple the polarization state and azimuthal angle variables.

A system, utilizing focused beam to implement simultaneous multi-angle measurement, has been described in U.S. Pat. No. 6,429,943 to Opsal et al. U.S. Pat. No. 6,429,943 describes using incident light focused on the sample by a large numerical aperture lens with the light beam center normal to the sample surface. The light beam in U.S. Pat. No. 6,429,943 when a light beam center is normal to the sample surface 62 is would therefore cause a spot 15 on the surface 62 of the sample 10. Meanwhile, in the example of FIGS. 1A and 1C, illustrated also by U.S. Pat. No. 5,166,752 to Spanier et al., the disclosure of which is hereby incorporated by reference, the center 66 of the focused light beam 21 is proposed to be off-normal, typically around 50 degrees off-normal (e.g., the incidence angle 64, $\theta_i$, would be 50 degrees). This off-normal arrangement is represented in FIG. 1C in x-y plane portion 101, where elliptical measurement spot 11 produced by an off-normal beam as in U.S. Pat. No. 5,166,752, and as represented by FIGS. 1A-1C, is shown compared to a spot 15 produced by a normal beam as described in U.S. Pat. No. 6,429,943. The off-normal arrangement in U.S. Pat. No. 5,166,752 and in FIGS. 1A-1C provides incident angles 64, $\Gamma_i$, up to 70 degrees, and such values of incident angles 64, $\theta_i$, are known to be more sensitive to thin multilayered films, to thin layers covering periodic structures, and to thin space layers formed on the side of poly-silicon gate electrode lines; see Thompson, et al., "A Logic Nanotechnology Featuring Strained-Silicon", IEEE Electron Device Letters, Vol. 25, No. 4 (April 2004).

The cone of angles of incidence of focused light beam 21 is a function of the focusing optic 4. In one embodiment, the focusing optic 4 is a refractive optical element or a combination of refractive optical elements. In another embodiment, the focusing optic 4 is a reflective optical element or elements such as, for example, a Schmidt-Cassegrain optical arrangement or a portion thereof In yet another embodiment, the focusing optic 4 may be a combination of refractive and reflective optical elements such as, for example, a catadioptric lens or a portion thereof. As each of the foregoing examples of focusing optic 4 are known by those skilled in the art as being interchangeable with one another, the present system is illustrated and described using only refractive optics.

The absolute range of angles of incidence is relatively large and may extend from near 0° to near 90°. The range of the cone of angles of incidence provided by focusing optic 4 is a function of its numerical aperture and may be as large or as small as is useful or possible given the constraints of optical design. In one embodiment the range of the cone of angles of incidence is at least 30° all told or ±15° to either side of the principal optical axis 66 of focused light beam 21. As an example, using an angle of incidence for the principal optical axis 66 of 50°, an absolute range of angles of incidence of about 35° to 65° may be obtained. As can be seen, by varying the optical design of the focusing optic 4 and by positioning principal optical axis 66 thereof in a desired location, many different ranges and orientations of angles of incidence may be obtained.

In addition to providing a simultaneous range of angles of incidence, focusing optic 4 may also provide a simultaneous range of azimuthal angles, Φ. Where the focusing optic 4 is symmetrical about the principal optical axis 66, the range of azimuthal angles Φ will be substantially the same as the range of angles of incidence. In some embodiments however, focusing optic 4 may be asymmetric with respect to the optical axis 66, such as where the focusing optic is a section of a reflective or catadioptric design. In these embodiments, the range of azimuthal angles may differ from the range of angles of incidence. As seen in FIG. 1C, the x-axis defines a principal azimuthal axis.

Characterization, including thickness and/or periodicity measurements of submicron structures (e.g., periodic structure 9) and thin film layers deposited under, on top, or around the structures, is performed by illuminating the structures and thin film layers with the focused light beam 21 of monochromatic light, and by detecting the light reflected by the structure with the detector array 7.

Characteristics of the thin films and/or structures on a sample 10 are determined using the measured signals 51 which are then compared to the predicted model values obtained by the solution of the scattering problem for the model of the structure. Model parameters (e.g., as defined by the measured signals 51) providing the best fit to the measured parameters constitute a measurement result. Model calculations require some preliminary knowledge of the dispersion properties of the materials comprising the structure and the geometry of the structure itself. In addition to standard interpolation and extrapolation techniques, analysis can be accomplished by the use of conventional non-linear optimization techniques such as the Levenberg-Marquardt algorithm, or a variety of other techniques, including locating the best match in the pre-calculated multi-dimensional libraries of the modeled Rp/Rs, for a multitude of combinations of the model parameters values, as described for instance in the following references, the disclosures of which are hereby incorporated by reference: U.S. Pat. No. 6,429,943 to Opsal et al.; U.S. Pat. No. 6,713,753 to Rovira et al.; and U.S. Pat. No. 6,721,052 to Zhao et al.

In some embodiments, a model is created using the nominal dimensions of a structure, i.e. layers and objects such as gratings, lines and the like, provided by a semiconductor device designer. Keeping in mind that process variations may change the dimensions of the structures on a sample 10, it is useful to verify the dimensions of a structure so as to optimize the model itself. This may be accomplished by using system 100 to obtain dimensional data such as layer thickness from a metrology site of a sample 10. Where the structures of interest are substantially transparent, an ellipsometer (such as system 100) may be used to obtain dimensional data. Alternatively, a separate ellipsometer 101 may be used to obtain the required dimensional data at the same metrology site simultaneous with a measurement by system 100 or at different metrology sites or at different times as system 100. Where one or more layers of a structure are sufficiently opaque or absorptive of incident light such that an ellipsometer is unable to obtain useful optical or dimensional data, a metrology system 101 such as picosecond ultrasonic metrology system or an X-Ray based metrology system may be used to obtain useful dimensional data, such as, for example layer thickness, though other dimensional data and characteristics of materials may also be obtained and utilized. Note that an ellipsometer is capable of obtaining dimensional data such as layer thickness in opaque materials only to a depth of approximately 200 to 300 angstroms. Accordingly, if a layer or structure fashioned of opaque materials is thicker than 200-300 angstroms, an ellipsometer will not provide any dimensional data. Dimensional data such as layer thickness may be used directly to modify the model used in the scatterometry metrology process. Alternatively, dimensional data such as layer thickness may be used to modify the predicted results output by the model. In either case, dimensional data may be used to correct or optimize the results obtained by a system 100.

Scatterometry systems for measurements of periodic structures for semiconductor manufacturing process metrology have been described in, e.g., U.S. Pat. No. 6,483,580 to Xu et al., U.S. Pat. No. 6,721,052 to Zhao et al., U.S. Pat. No. 6,657,736 to Finarov et al., and U.S. Pat. No. 6,713,753 to Rovira et al., the disclosures of which are hereby incorporated by reference. The systems in these cited patents are based, e.g., on spectroscopic ellipsometry or reflectometry measurements performed by measuring reflectances and/or ellipsometric functions for a range of light wavelengths at a single incidence angle. In these cases, accuracy relies on the accurate knowledge of the complex refractive indices of the materials of the structure across the broad wavelength spectrum.

The accuracy of multi-angle of incidence and azimuth measurements using light at a one or a number of discrete wavelengths values requires knowledge of the material of the sample complex refractive indices only at these wavelengths. Independent measurements at the same discrete wavelengths on simpler samples can be used to establish refractive indices at the required wavelengths of the materials in the samples. Consequently, in an exemplary embodiment herein, independent measurements of a sample are taken at a multitude of discrete wavelengths and data from the measurements are combined and analyzed. Using lasers (e.g., as coherent light sources 1) as a source of monochromatic light makes this exemplary measurement system faster and more stable in comparison to conventional spectroscopic systems utilizing continuous spectrum light sources. Further, using more than just one light wavelength provides information necessary to obtain more structural information to cover a wider range of parameter variation, and also to resolve possible solution ambiguities. Performing multiple measurements including using multiple coherent light sources 1 is described in further detail in reference to FIGS. 2 through 4. It should be noted that the coherent light sources 1 will typically be lasers but could also include laser light emitting diodes (LEDs) and other devices able to produce coherent light. In some embodiments, partially or completely incoherent light sources arranged to output substantially a single wavelength may be used. An example of one such source is an LED. Further, by incorporated appropriate filters (not shown) or a monochromator (not shown) positioned between the light source 1 and the polarizer 2, broad band light sources may also be used to obtain suitable incident light beams 21.

It is beneficial for the scatterometry measurements to cover as many periods of the sample structure as possible, as the models used to extract the structure parameters from the measurement assume infinite number of the grating periods covered by the incident light. The normal incidence system in U.S. Pat. No. 6,429,943 to Opsal et al. has a small circular measurement spot 15 on the sample. U.S. Pat. No. 6,429,943 describes a proposal for the spot 15 to be scanned across the periodic structure 9 in order to cover more periods of the periodic structure 9. The exemplary system of FIGS. 1A-1C, however, provides an elliptical measurement spot 11 on the sample 10, and such elliptical measurement spot 11 can be arranged to cover more periods of the periodic structure, as shown in FIG. 1C. That the elliptical measurement spot 11 provides extra periods 70 therefore can provide improved results as compared to the results provided when the measurement spot 15 is used. In one embodiment, a metrology spots sites on a sample 10 may be approximately 50 microns square. As semiconductor device sizes continue to shrink, so do metrology site dimensions. For example, newer semiconductor devices may include metrology sites of approximately 30 microns square. Metrology spots 15 may be any suitable shape including, but not limited to, square, rectangular, triangular, polygonal, circular, elliptical, or any other shape that a designer finds suitable.

The data processing and control system 8 typically will include one or more processors (not shown) coupled to one or more memories (not shown). The data processing and control system 8 may include, for example, multiple discrete, networked computer systems. The data processing and control system 8 will typically include one or more software portions (not shown) comprising instructions suitable for execution by the one or more processors of the data processing and control system 8. The software portions may also be embodied as a signal bearing medium tangibly embodying a program of machine-readable instructions executable by the data processing and control system 8 (e.g., one or more processors thereof) to perform operations described herein. Note that a processor will typically be a general-purpose processor but could also be a digital signal processor, data processor, or a processing unit custom designed to efficiently generate modeled scattering data.

Similar to measuring the sample 10 at different wavelengths, measuring the sample 10 at different orientations relative to the incidence plane 60 of the ellipsometer provides more information about the periodic structure 9, and also provides selective sensitivities to different structure parameters. For the orientations of the periodicity direction 71 (see FIG. 1C) when the lines 92 of the periodic structure 9 are either parallel or perpendicular to the incidence plane 60 of the ellipsometer, no mixing between the S- and P-polarizations should occur, and the measurements are therefore less subject to variability in sample orientation. In FIG. 1B, the periodicity direction 71 is shown parallel to the x axis (i.e., perpendicular to the y axis) and parallel to the incidence plane 60. Lines 92 run perpendicular to the periodicity direction 71. Other orientations of the periodicity directions 71 may also be used.

In the example of FIG. 1A, the sample 10 is placed on a sample platen 12 that has the ability to orient the sample 10 in a number of orientations to create a number of corresponding periodicity directions. In an exemplary embodiment, the orientations are defined by the periodicity direction 71. The sample platen 12 may also provide translational movement (e.g., movement along the x axis and/or y axis), and/or rotational movement (e.g., movement relative to the center of the sample platen), and/or vertical movement (e.g., movement in the x axis). Such movement may be performed for sample positioning, such that the measurement spot 11 is focused on a particular periodic structure, or for focusing. Further, the sample 10 may be positioned such that the largest number of periods for the periodic structure 9 is positioned within the focused measurement spot 11.

Figure 2:
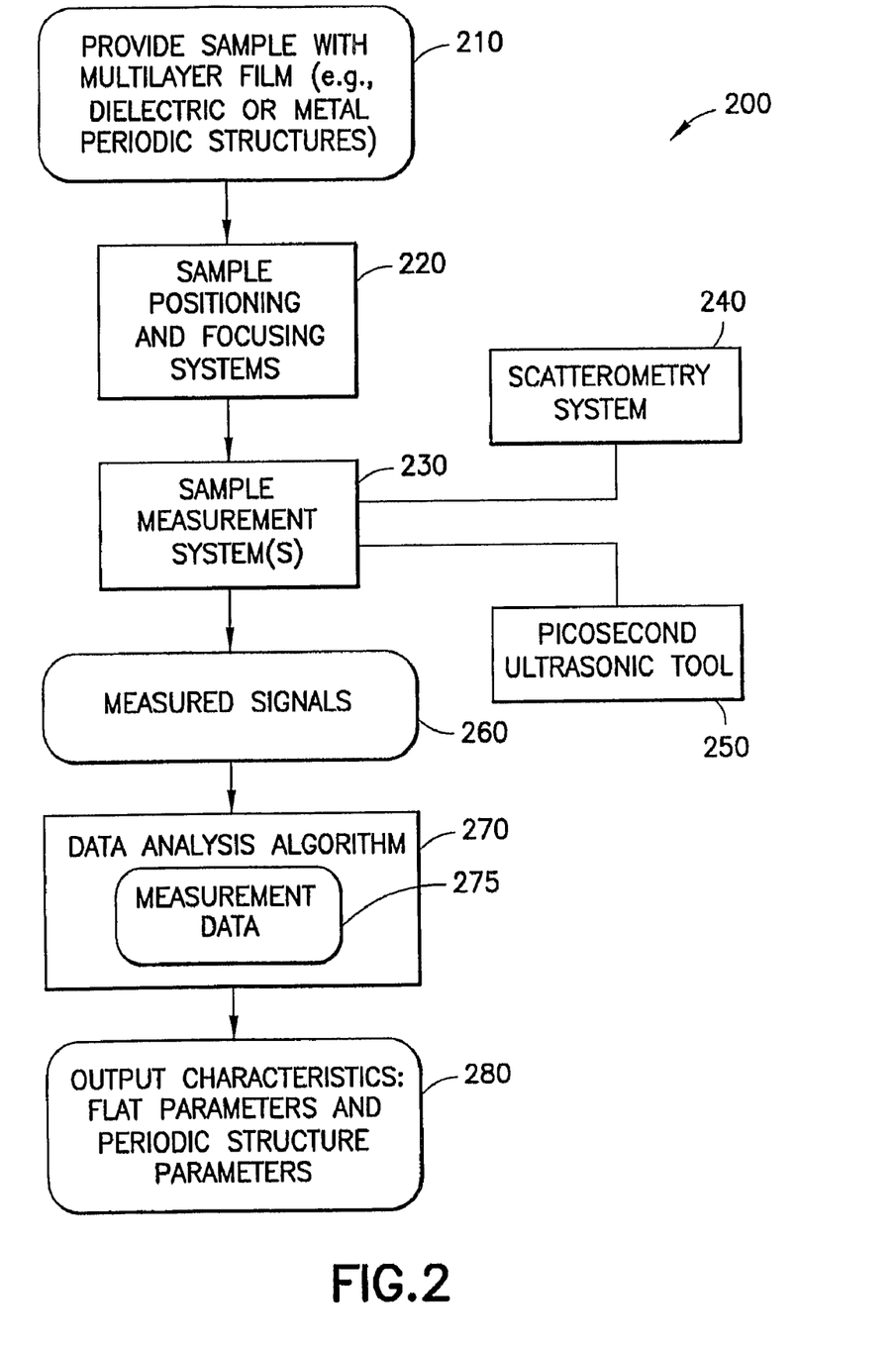
FIG. 2 is an exemplary chart of a measurement flow diagram.

Referring now to FIG. 2 along with reference when needed to FIGS. 1A-1C, a chart 200 is shown in FIG. 2 of a measurement flow diagram is shown. Chart 200 is a simplified diagram of certain exemplary steps taken, including systems and inputs, outputs, and internal data used for such systems, for measurement of a sample 10. Reference numerals 210, 260, 275 and 280 are related to inputs, outputs, and internal data, whereas reference numerals 220, 230, 240, 250, and 270 are related to systems.

Reference 210 represents a step of providing a sample 10. The sample 10 includes a multilayer film, typically including dielectric or metallic periodic structures. It should be noted that "flat". measurements could also be taken, where flat measurements are taken on "flat" portions of samples or a "flat" sample. A "flat" portion of a sample is a flat area of a sample 10 that does not contain structures (e.g., does not contain a periodic structure 9). A "flat" sample 10 is a sample 10 that does not contain structures (e.g., does not contain a periodic structure 9).

Reference 220 indicates that sample positioning and focusing system(s) position and focus the sample. Positioning includes, e.g., ensuring that the measurement spot 11 is placed at a particular portion of the sample 10. For example, a particular periodic structure 9 or a set thereof could be aligned with and illuminated by the measurement spot 11. As another example, a portion of the sample 10 that is flat is aligned with and illuminated by the measurement spot 11. Positioning may also include positioning for other measurement systems, such as a picosecond ultrasonic tool.

Reference 230 indicates that sample measurement systems are used to measure characteristics of the sample 10. In particular, one or more scatterometry systems 240 (e.g., such as scatterometry system 100 of FIG. 1A, which can include ellipsometry and reflectometry systems) are used to produce measured signals 260 (e.g., measured signals 51 of FIG. 1A) corresponding to the portion of the sample 10 that is illuminated. Reference 270 indicates that a data analysis algorithm operates to analyze the measured signals 260 to determine output characteristics 280 of the sample 10. In an exemplary embodiment, the data analysis algorithm 270 operates on the measured signals 260 to create measured data 275. For instance, the data analysis algorithm 270 converts analog measured signals 260 to digital measurement data 275. As another example, the data analysis algorithm 270 maps the measured signals 260 into measurement data 275. In another exemplary embodiment, the measured signals 275 do not need to be operated on and the measured signals 275 are used without creating measurement data 275. The output characteristics 280 of the sample 10 could include thickness of thin-films (e.g., in both in flat portions of the sample and portions containing periodic structures 9) and parameters for periodic structures 9 such as structure dimensions including pitch, critical dimension, spacer sizes and width of structures such as gate electrodes.

Another exemplary embodiment includes measuring the sample 10 by using both the scatterometry system(s) 240 (e.g., an ellipsometer) along with a picosecond ultrasonic metrology tool 250, where the scatterometry system(s) 240 makes flat measurements (i.e., measurements on a flat portion of the sample 10 or using a flat sample) and the picosecond ultrasonic tool 250 makes flat measurements, and the measured signals 260 (e.g., or measurement data 275) are combined in data analysis algorithm 270 to produce improved results in characteristics 280 of the sample 10. As another example, the scatterometry system(s) 240 makes structured measurements (i.e., measurements on a portion of the sample 10 having a periodic structure 9) and the picosecond ultrasonic tool 250 makes structured measurements, and the measured signals 260 (e.g., or measurement data 275) are combined in data analysis algorithm 270 to produce improved results in characteristics 280 of the sample 10. FIG. 1D illustrates one embodiment of a combination of system 100 with a second system 101. In this embodiment, measurements of characteristics of a sample 10 are captured using one or more metrology systems 101 other than system 100. These characteristics are then used to improve the accuracy of the measurement of a sample 10 under test by the system 100. For example, an index of refraction of a material or sample may be obtained using a picosecond ultrasonic metrology tool. Such a metrology tool is described in U.S. Pat. Nos. 6,175, 416 and 7,050,178, which are hereby incorporated by reference. An index of refraction may also be obtained using a separate ellipsometer, spectroscopic or monochromatic, a reflectometer, or a refractometer, among others. Other characteristics that may be obtained using metrology or inspection systems other than system 100 and used to improve the accuracy of a measurement include transmittance, surface reflectances, and any other useful optical property of a material of a sample 10. System 101 may be a picosecond ultrasonic metrology system, a monochromatic or spectroscopic ellipsometer, a reflectometer, a macro or micro defect inspection system or any other useful metrology or inspection system. In another embodiment, the system 100 may be operated as an ellipsometer either prior to or simultaneous with its function as a scatterometer. In this embodiment, ellipsometric measurements of characteristics of the sample are used to modify the model and/or correlation between measured data and the model to ensure proper and efficient functioning.

Figure 3:
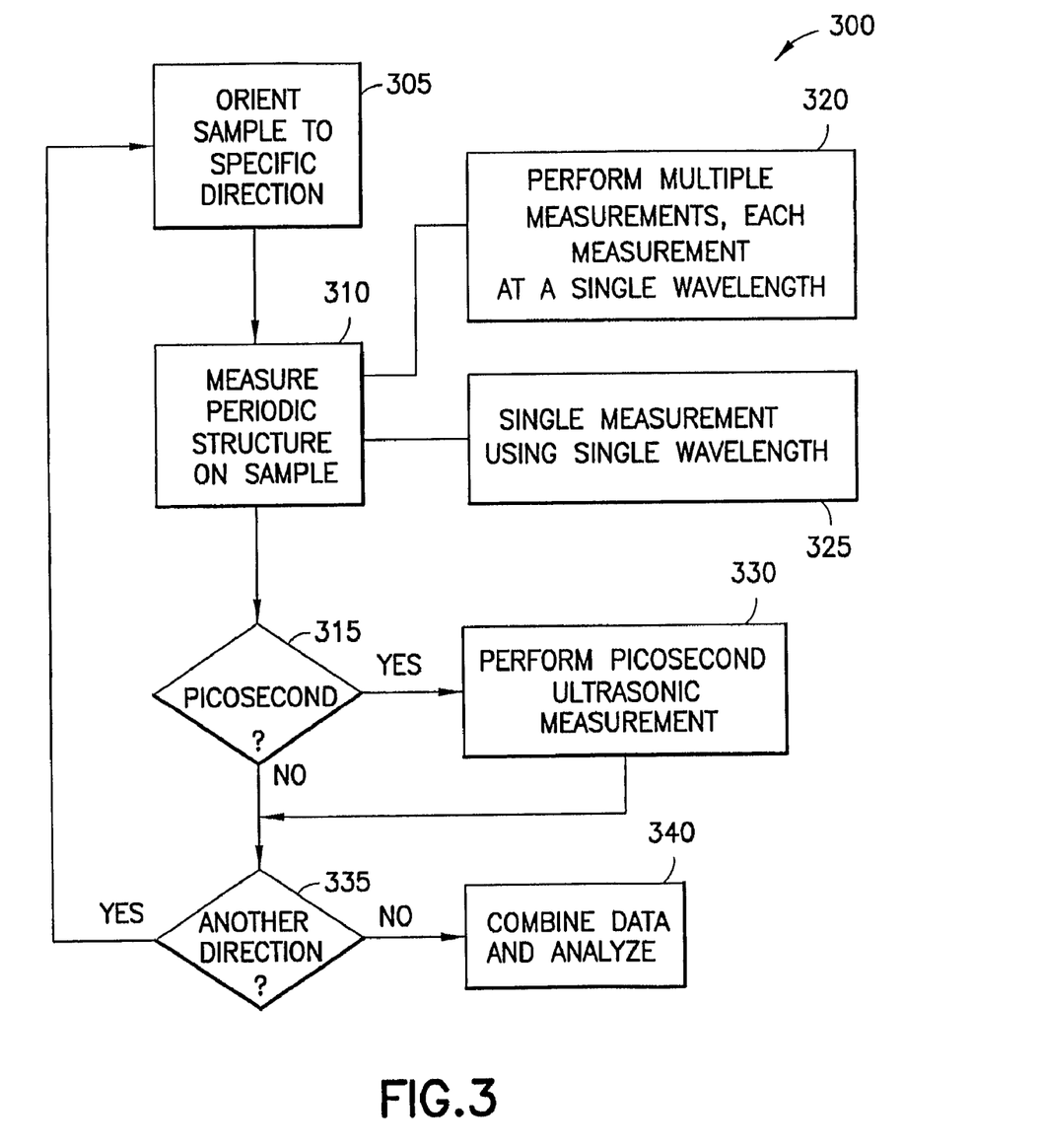
FIG. 3 is a flowchart of an exemplary method for performing multiple measurements including focused beam scatterometry for characterization of samples including periodic structures.
Figure 4:
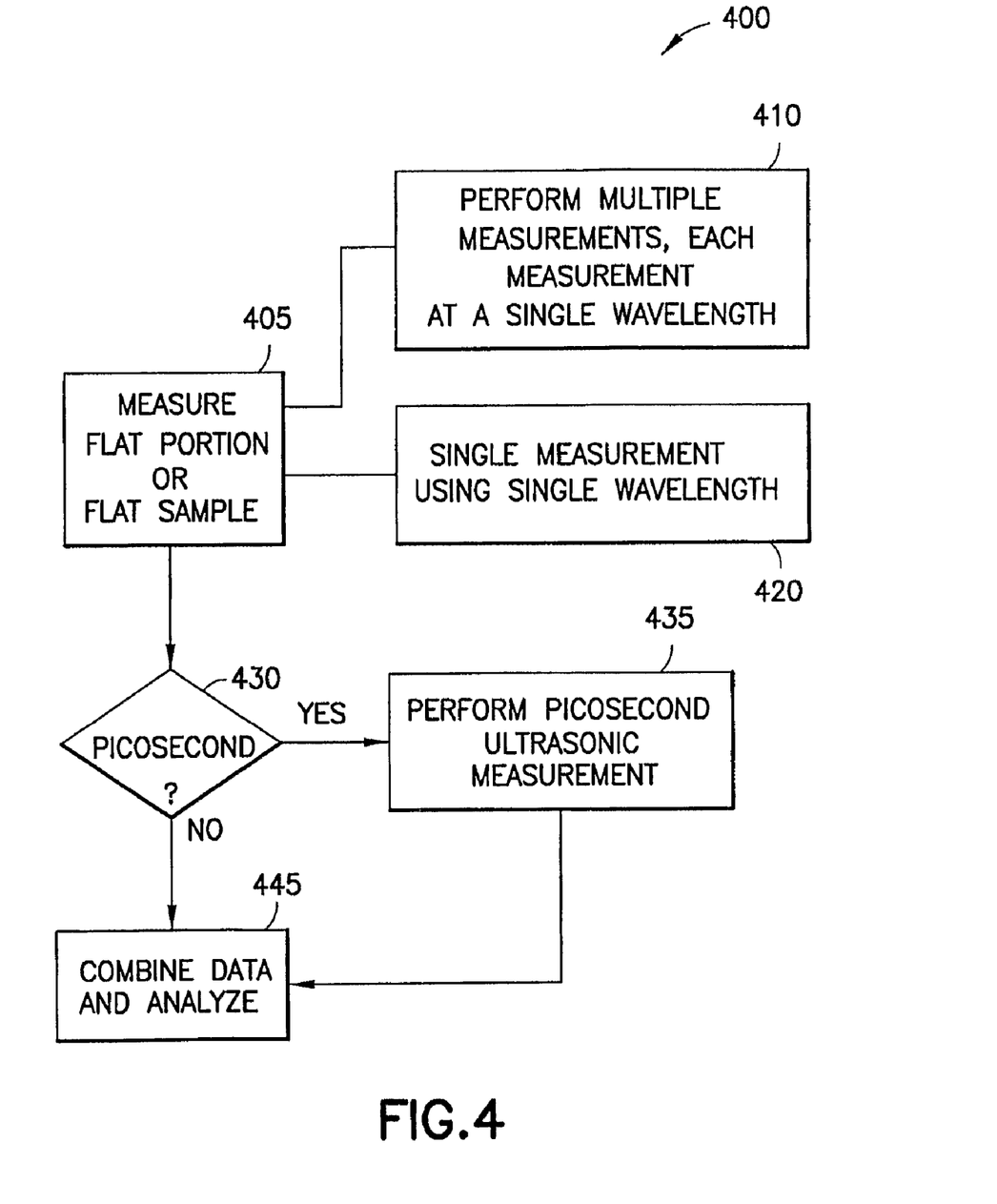
FIG. 4 is a flowchart of an exemplary method for performing multiple measurements including focused beam scatterometry for characterization of "flat" samples.

Referring now to FIG. 3 with appropriate reference to previous figures, a flowchart is shown of an exemplary method 200 for performing multiple measurements including focused beam scatterometry for characterization of samples including periodic structures. Method 300 starts in step 305, when the sample 10 is oriented to a specific direction. For instance, the sample 10 could be oriented such that periodicity direction 71 (see FIG. 1B) is parallel to the incidence plane 60. In FIGS. 3 and 4, the term "measurement data" includes one or more of measurement data 275 or measured signals 260.

In step 310, the periodic structure 9 on the sample 10 is measured. Steps 320 and 325 are two alternative techniques for measuring the periodic structure 9 in step 310. In step 320, multiple measurements are performed, each measurement at a single wavelength. Each single wavelength is created by a coherent light source 1. Alternatively, in step 325, a single measurement is performed using a single wavelength.

In step 315, it is determined if a picosecond ultrasonic measurement is to be performed. If so (step 315=YES), a picosecond ultrasonic measurement is performed in step 330. If not (step 315=NO) or after the picosecond ultrasonic measurement has been performed in step 330, then it is determined whether another direction is to be used.

If so (step 335=YES), the sample 10 is oriented to another specific direction. For instance, the sample 10 could be reoriented such that periodicity direction 71 (see FIG. 1B) is placed 90 degrees from the original periodicity direction 71 when step 305 was first performed. In the example of step 305 given above, the periodicity direction 71 could be changed from parallel (the first time step 305 is performed) to the incidence plane 60 to perpendicular (the second time step 305 is performed) to the incident plane 60. Periodicity directions 71 other than parallel and perpendicular to the incidence plane 60 may also be used. It should be noted that the periodicity directions 71 could be characterized by an angle, if desired. For instance, a periodicity direction 71 parallel to the incident plane 60 could be considered to be at zero degrees and a periodicity direction 71 perpendicular to the incident plane 60 could be considered to be at ninety degrees. Using this characterization, angles between zero and 90 degrees would typically be used for measurements.

If there is no other direction to be examined (step 335=NO), in step 340, the measurement data are combined from the steps 320, 325, and 330 that were performed in method 300 and from the periodicity direction(s) 71 that were used during the method 300. Method 300 allows many different combinations of measured data to be analyzed in step 330. For instance, single measurements using single wavelengths (step 325) could be performed at each of two different periodicity directions 71 and the measurement data from these two measurements combined in step 340. As another example, single measurements using single wavelengths (step 325) could be performed at each of two different periodicity directions 71 and these two measurements could be combined with two measurements of the picosecond ultrasonic measurement (step 330), each picosecond ultrasonic measurement performed for a periodicity direction 71 of the sample 10.

As a further example, multiple measurements could be performed, each measurement performed at a single wavelength (step 320), but these measurements would only be performed at a single periodicity direction 71 of the sample. These measurements would be combined in step 340. As yet another example, the measurements of both step 320 and 330 would be combined in step 340, but the measurements for steps 320 and 330 would only be performed at a single periodicity direction 71 of the sample. These examples are only some of the many variations possible in method 300.

Turning to FIG. 4 with appropriate reference to preceding figures, FIG. 4 is a flowchart of an exemplary method 400 for performing multiple measurements including focused beam scatterometry for characterization of "flat" portions of a sample or "flat" samples. As described above, a "flat" portion of a sample is a flat area of a sample 10 that does not contain structures (e.g., does not contain a periodic structure 9), and a "flat" sample 10 is a sample 10 that does not contain structures (e.g., does not contain a periodic structure 9). Steps in method 400 are similar to method 300, so these steps will not be explained in detail in reference to FIG. 4.

Method 400 begins in step 405, when the flat portion of sample 10 or a flat sample 10 is measured. Steps 410 and 420 are two alternative techniques for measuring the periodic structure 9 in step 405. In step 410, multiple measurements are performed, each measurement at a single wavelength. Each single wavelength is created by a coherent light source 1. Alternatively, in step 420, a single measurement is performed using a single wavelength.

In step 430, it is determined if a picosecond ultrasonic measurement is to be performed. If so (step 430=YES), a picosecond ultrasonic measurement is performed in step 435. If not (step 430=NO) or after the picosecond ultrasonic measurement has been performed in step 435, measurement data from any step 410, 420, and 435 performed during method 400 is combined and analyzed. Unlike method 300, method 400 does not provide steps for measuring data at different orientations of periodic structures 9, as no such periodic structures 9 are being measured in method 400. However, as with method 300, method 400 allows many different combinations of measured data to be combined and analyzed (see step 445).

For instance, a single measurement using a single wavelength (step 420) could be performed and combined (step 445) with a measurement of the picosecond ultrasonic measurement (step 435). As another example, step 410 could be performed without performing step 435 and the measurement data from step 410 combined in step 445. As yet another example, the measurements of both step 410 and 435 would be combined in step 440. These examples are only some of the many variations possible in method 400.

In another embodiment, an ellipsometer takes measurements at multiple angles of incidence and at a few (e.g., 1-6) wavelengths successively to characterize periodic structures, with measurements at multiple angles of incidence ranging from approximately 40 to approximately 70 degrees, performed simultaneously by means of a focused incident beam, which is collected and projected on a detector array after scattering from the sample. Light sources may include coherent or incoherent sources and may be broadband or substantially monochromatic as suggested above.

In some embodiments, measurements may be performed at a few orientations of the periodicity direction 71 and the incidence plane 60 of the scatterometry system (e.g., ellipsometer). Typical measurements would be zero and 90 degrees for the periodicity direction 71 relative to incidence plane 60. In some embodiments however, it is useful to take multiple measurements at orientations of the periodicity direction 71 that are not 0° or 90°. In one example, an "ideal" orientation of the periodicity direction 71 is calculated and multiple measurements at orientations of the periodicity direction 71 at or near the calculated ideal are obtained to verify that the calculated ideal is an optimal orientation. This verification process may take place for each measurement spot or site for each sample or may be part of a recipe set up process that occurs prior to processing a lot of samples 10 and may occur only a single time or only a few times during the recipe set up process.

Combining measurement data from different orientations (angle of incidence and azimuthal angles) and wavelengths and simultaneously comparing these values to a model in order to find the optimal model parameters has also been found to be useful. In one exemplary embodiment, combined measurements are be fitted to the model all together with proper weighting factors, the weighting factors being correlated to various aspects or characteristics of the sample. For example, in some embodiments, a parameter or characteristic may be more sensitive to an azimuthal angle. Accordingly, more weight may be given to differentiation of data based on azimuthal angle than to angle of incidence.

In another exemplary embodiment, a multiple-step solution may be performed, where different measurements or their combinations are used to determine one or more of the model parameters. In the following steps, these model parameters from the first step are then used as fixed at the resulting values from the first step. The following steps involve a different set of measured data derived from system 100 or system 101. For instance, a model might be used to determine Parameters A, B, and C. A first step would fix Parameter A, while additional steps would use the fixed Parameter A when determining Parameters B and C. As an additional example, ultrasonic and ellipsometric measurements may be sensitive to different aspects of periodic and non-periodic structures, and also to different parameters. Thus, illustratively, ultrasonic measurements could be used to determine depth (e.g., thickness) of the structures, and then the fixed depth value would be used for processing ellipsometry data in order to extract thicknesses of the thin films deposited over the structures.

FIG. 1D illustrates a system 101 that takes a measurement of a measurement spot or site that is also addressed by system 100. In other embodiments, systems 100 and 101 may be arranged to measure spots that are spaced apart from one another though it is often the case, though not always, that both systems will measure the same measurement spots. Further, systems 100 and 101 may also be offset from one another azimuthally and in this configuration may be arranged to measure the same measurement spot simultaneously or may be laterally offset from one another. As will be appreciated, data derived from system 100 and 101 may be processed separately, but are often processed together to optimize the measurement process.

It is contemplated that measurement swill be taken by system 100 and/or system 101 at various wavelengths. This may occur simultaneously as in the case of a spectroscopic ellipsometer or sequentially as with an ellipsometer that uses multiple independent light sources having substantially a single wavelength.

In one embodiment, the detector array 7 may be one or more one dimensional detectors such as an optical multichannel analyzer (OMA). In this embodiment, the detector 7 would output a single intensity data value for each angle of incidence. In order to obtain data concerning multiple azimuthal angles, the sample 10 (or the system 100) would have to be rotated with respect to one another. Further, where data at multiple wavelengths were desired, data at multiple wavelengths would be captured at each azimuthal angle.

In another embodiment, multiple OMAs may be aligned the one next to the other such that each OMA in an array of OMAs will output multiple intensity data values, specific angles of incidence, each OMA being associated with a single azimuthal angle. In effect, an array of OMAs will act in much the same way as a two dimensional CCD array.

As suggested in the preceding paragraph, a two dimensional CCD array may also be used. In such an array each dimension may be mapped to a different parameter such as angle of incidence, azimuthal angle or wavelength. In one embodiment the system 100 operates as an ellipsometer, horizontal rows of the CCD may be arranged to output data for a single angle of incidence, the multiple horizontal rows each being related to a separate angle of incidence. In this embodiment, the vertical rows of the CCD array may be mapped to either an azimuthal angle or, with the provision of a suitable prism, grating or other spectroscopic device between the analyzer 6 and the detector 7, to a wavelength.

Receiving optic 5 collects reflected beam 22, re-collimates it and directs the collimated light onto the detector 7. As will be appreciated from the preceding paragraph, the collimated beam includes separate angle of incidence and azimuthal angle components that are mapped onto the detector array 7. Stops, slits and/or apertures (not shown) may be included in system 100 to limit the extent of beam 23 that is incident upon the detector array 7. The capture of the whole reflected beam 22 would thus provide information important to determine the Rp/Rs for different incidence angles and structure orientations. Such arrangement may be alternative to the described embodiment above that employs multiple ellipsometer systems focusing at the same spot.

The foregoing description has provided by way of exemplary and non-limiting examples a full and informative description of the best techniques presently contemplated by the inventors for carrying out embodiments of the invention. However, various modifications and adaptations may become apparent to those skilled in the relevant arts in view of the foregoing description, when read in conjunction with the accompanying drawings and the appended claims. All such and similar modifications of the teachings of this invention will still fall within the scope of this invention.

Furthermore, some of the features of exemplary embodiments of this invention could be used to advantage without the corresponding use of other features. As such, the foregoing description should be considered as merely illustrative of the principles of embodiments of the present invention, and not in limitation thereof.

The invention claimed is:

1. An ellipsometric metrology tool for optically measuring characteristics of a substrate comprising:
   at least one light source adapted to output a beam of incident light;
   a first optical element for focusing the incident light onto a metrology site of the substrate having a periodic structure formed thereon at a plurality of incident angles and at a plurality of azimuthal angles, an optical axis of the first optical element being inclined at an oblique angle with respect to a plane of the substrate;
   a second optical element for directing reflected light reflected from the metrology site to a detector, the detector output being at least partially correlated to a polarization state of the incident light, a phase shift of the reflected light, at least one of the plurality of incident angles, and at least one of the plurality of azimuthal angles of the incident light with respect to the metrology site.

2. The ellipsometric metrology tool of claim 1 wherein the detector is a two dimensional array of light sensitive elements, each element outputting a light intensity value that is at least partially correlated to an angle of incidence and azimuthal angle of the incident light with respect to the metrology site and a wavelength of the incident light.

3. The ellipsometric metrology tool of claim 1 wherein the at least one light source comprises a plurality of light sources that each output substantially monochromatic light of a different wavelength.

4. The ellipsometric metrology tool of claim 1 further comprising a polarizer and a compensator positioned between the at least one light source and the first optical element and an analyzer positioned between the second optical element and the detector, at least one of the polarizer, compensator and analyzer rotating about an optical axis of the metrology tool at a known rate.

5. The ellipsometric metrology tool of claim 1 wherein the output of the detector is a function of at least two variables selected from a group consisting of at least one of the plurality of incident angles, at least one of the plurality of azimuthal angles, a wavelength, the polarization state of the incident light, and an index of refraction.

6. The ellipsometric metrology tool of claim 1 further comprising a control system having a library of predicted solutions for a plurality of models of the periodic structure and a fitting module for correlating the output of the detector with at least one solutions in the library to identify a likely substrate configuration that would produce the output of the detector.

7. The ellipsometric metrology tool of claim 6 wherein the predicted solutions are a function of at least two variables selected from a group consisting of at least one of the plurality of incident angles, at least one of the plurality of azimuthal angles, a wavelength, the polarization state of the incident light, a polarization state of reflected light and an index of refraction.

8. The ellipsometric metrology tool of claim 1 wherein the incident light is incident upon the metrology site of the substrate at a range of incident angles of about +/−30° of the optical axis of the metrology tool.

9. The ellipsometric metrology tool of claim 1 wherein the incident light is incident upon the metrology site of the substrate at a range of azimuthal angles of about +/−30° of an optical axis of the metrology tool.

10. The ellipsometric metrology tool of claim 1 wherein the first optical element is selected from at least one of a refractive optical element and a reflective optical element.

11. A method of monitoring a fabrication process comprising:
    directing a beam of light at a metrology site of a sample having a periodic structure formed thereon at a range of oblique angles of incidence and a range of azimuthal angles, the respective ranges of the angles of incidence and azimuthal angles being disposed about an oblique optical axis, wherein the beam of light is of a known polarization state;
    collecting the beam of light upon reflection from the metrology site of the sample and directing it to a detector; and,
    outputting from the detector at least one array of data values that are at least partially correlated to the polarization state of the beam of light, a phase shift in the beam of light upon reflection, at least one of the angles of incidence of the beam of light and at least one of the azimuthal angles of the beam of light.

12. The method of claim 11 further comprising:
    modifying a wavelength of the beam of light incident on the sample.

13. The method of claim 11 further comprising:
    directing the beam of light at the metrology site at least two primary azimuthal angles, and determining an optimal primary azimuthal angle based on measurement results obtained at the at least two primary azimuthal angles.

14. The method of claim 11 further comprising:
    deriving from the at least one array of data values at least one parameter and, comparing the at least one parameter with at least one pre-calculated parameter to identify at least one characteristic of the sample.

15. The method of claim 11 further comprising:
    directing the beam of light at the metrology site of the sample at a simultaneous range of azimuthal angles measured at +/−20° of a principal optical axis of the beam of light.

16. The method of claim 15 further comprising:
    identifying from a model of the sample an optimal azimuthal angle of the beam of light and, comparing data output by the detector at the optimal azimuthal angle of the principal angle of the beam of light with at least one other azimuthal angle of the principal angle of the beam of light to validate the model.

17. The method of claim 16 further comprising:
    updating the model to account for an offset between expected data and actual data obtained from the detector.

18. The method of claim 11 further comprising:
    forming a model based at least in part on a predicted characteristic of a sample;
    obtaining data concerning the predicted characteristic of the sample; and,
    forming the model based on the obtained data concerning the predicted characteristic.

19. The method of claim 18 wherein the predicted characteristic is an index of refraction of the sample.

20. The method of claim 18 wherein the model is for use with a first metrology system and at least one data concerning the predicted characteristic is obtained from a second metrology system.

21. The method of claim 20 wherein the first metrology system is an ellipsometer and the second metrology system is selected from a group consisting of a picosecond ultrasonic metrology system, a profilometer, a polarimeter, a reflectometer, a spectrometer, an ellipsometer, Xray reflectometer, an Xray fluorescent metrology tool and a defect inspection system.

* * * * *